United States Patent
Liang et al.

(10) Patent No.: US 9,788,795 B2
(45) Date of Patent: Oct. 17, 2017

(54) MAGNETIC RESONANCE IMAGING METHOD

(71) Applicant: The Research Foundation for The State University of New York, Albany, NY (US)

(72) Inventors: Jerome Zhengrong Liang, Stony Brook, NY (US); Qin Lin, Stony Brook, NY (US)

(73) Assignee: The Research Foundation for The State University of New York, Albany, NY (US)

( * ) Notice: Subject to any disclaimer, the term of this patent is extended or adjusted under 35 U.S.C. 154(b) by 111 days.

(21) Appl. No.: 14/784,192

(22) PCT Filed: Jun. 6, 2014

(86) PCT No.: PCT/US2014/033990
§ 371 (c)(1),
(2) Date: Oct. 13, 2015

(87) PCT Pub. No.: WO2014/193552
PCT Pub. Date: Dec. 4, 2014

(65) Prior Publication Data
US 2016/0066856 A1     Mar. 10, 2016

Related U.S. Application Data

(60) Provisional application No. 61/811,427, filed on Apr. 12, 2013.

(51) Int. Cl.
G06T 7/00 (2017.01)
A61B 5/00 (2006.01)
(Continued)

(52) U.S. Cl.
CPC ............ *A61B 5/7214* (2013.01); *A61B 5/004* (2013.01); *A61B 5/055* (2013.01); *A61B 5/202* (2013.01);
(Continued)

(58) Field of Classification Search
None
See application file for complete search history.

(56) References Cited

U.S. PATENT DOCUMENTS

2004/0102695 A1   5/2004   Stergiopoulos et al.
2007/0165923 A1   7/2007   Shen et al.
(Continued)

FOREIGN PATENT DOCUMENTS

EP          2423701          2/2012

OTHER PUBLICATIONS

Lin, Q. Liang, Z. Li, H, Jamawalikar, S. Wang, Q. Phillips, B. Waltzer, W. Zawin, M. Harrington D., and He, X. "An Image Processing Approach to Compensate for the Bladder Wall Motion and Deformation in MR Cystography" 2011 IEEE Nuclear Science Symposium Conference Record.*
(Continued)

*Primary Examiner* — Kim Vu
*Assistant Examiner* — Molly Delaney
(74) *Attorney, Agent, or Firm* — The Farrell Law Firm, P.C.; John F. Gallagher, III (57) ABSTRACT

Provided is a method for compensating for tissue motion during magnetic resonance (MR) imaging, and an apparatus for use thereof. The method includes acquiring a plurality of short-time MR scan images; selecting a reference scan image from the acquired plurality of short-time MR scan images; defining a set of transformation images based on the acquired plurality of short-time MR scan images other than the selected reference scan image; registering the reference
(Continued)

scan image and the defined set of transformation images; calculating an average of aligned, registered images of the defined set of transformation images; and generating a motion-corrected image based on the calculated average.

15 Claims, 7 Drawing Sheets

(51) Int. Cl.
    *A61B 5/055*     (2006.01)
    *G01R 33/565*     (2006.01)
    *G06T 5/00*     (2006.01)
    *G06T 5/50*     (2006.01)
    *A61B 5/20*     (2006.01)
    *G06T 7/33*     (2017.01)
    *G06T 7/246*     (2017.01)
    *G01R 33/56*     (2006.01)

(52) U.S. Cl.
    CPC ........ *G01R 33/56509* (2013.01); *G06T 5/003* (2013.01); *G06T 5/50* (2013.01); *G06T 7/0014* (2013.01); *G06T 7/248* (2017.01); *G06T 7/337* (2017.01); *A61B 2576/00* (2013.01); *G01R 33/5608* (2013.01); *G06T 2207/10016* (2013.01); *G06T 2207/10088* (2013.01); *G06T 2207/30024* (2013.01); *G06T 2207/30096* (2013.01); *G06T 2210/41* (2013.01)

(56) References Cited

U.S. PATENT DOCUMENTS

| | | | |
|---|---|---|---|
| 2007/0276221 A1 | 11/2007 | Wamtjes | |
| 2010/0142778 A1* | 6/2010 | Zhuo | G06T 5/50 382/128 |
| 2016/0145185 A1 | 5/2016 | Baek et al. | |

OTHER PUBLICATIONS

PCT/ISA/210 Search Report issued on PCT/US2014/033990 (pp. 4).

PCT/ISA/237 Written Opinion issued on PCT/US2014/033990 (pp. 3).

\* cited by examiner

MAGNETIC RESONANCE IMAGING METHOD

PRIORITY

This application claims priority under 35 U.S.C. §119(e) to U.S. Provisional Patent Application No. 61/811,427, which was filed on Apr. 12, 2013, the entire disclosure of which is incorporated herein by reference.

BACKGROUND OF THE INVENTION

1. Field of the Invention

The present invention relates generally to a Magnetic Resonance (MR) imaging method. More particularly, the present invention relates to an MR imaging method that uses short-time scan acquisition and deformable registration to compensate for bladder motion during imaging.

2. Description of the Related Art

According to recent studies, over the last few decades, the incidence of bladder cancer has increased significantly and has become the fifth leading cancer incidence (after lung/bronchus, prostate, breast and colon) and the eighth leading cause of cancer-related deaths in the United States. Additionally, management of bladder cancer is a challenge due to high recurrence rate, e.g., as high as 80%, after local tumor resection. As can be appreciated, early detection of bladder cancer or other abnormality is crucial for improving patient prognosis and treatment.

Conventional fiber-optic cystoscopy (OCy) is an accurate method for diagnosis and surveillance of bladder cancer. OCy, however, is invasive, costly, provides a limited field of view for the clinician during use, and has been known to cause urinary tract infection.

MR imaging provides a non-invasive method for evaluating the bladder. Such a method typically uses short-time and/or long-time scanning protocols. Short-time scanning, however, suffers from low Signal-to-Noise Ratio (SNR), and long-time scanning can introduce motion artifacts resulting from T1 and T2 relaxations of the bladder due to urine inflow, colon motion, peristalsis, and lung breathing.

Therefore, a reliable, non-invasive and easy-performance method for bladder imaging and/or evaluation is needed.

SUMMARY OF THE INVENTION

In view of the above, an MR imaging method is provided that uses short-time scan acquisition and deformable registration to compensate for bladder motion during MR imaging. An aspect of the present invention provides a method for compensating for tissue motion during MR imaging. The method includes acquiring a plurality of short-time MR scan images; selecting a reference scan image from the acquired plurality of short-time MR scan images; defining a set of transformation images based on the acquired plurality of short-time MR scan images other than the selected reference scan image; registering the reference scan image and the defined set of transformation images; calculating an average of aligned, registered images of the defined set of transformation images; and generating a motion-corrected image based on the calculated average.

Another aspect of the present invention provides a method for compensating for tissue motion during MR imaging. The method includes acquiring a plurality of short-time MR scan images; selecting a reference scan image from the acquired plurality of short-time MR scan images; defining, using a first registration process, a first set of transformation images based on the acquired plurality of short-time MR scan images other than the selected reference scan image; defining, using a second registration process, a second set of transformation images based on the acquired plurality of short-time MR scan images other than the selected reference scan image; registering the reference scan image and the defined first and second sets of transformation images using the first registration process and the second registration process; calculating an average of aligned, registered images of the defined first and second sets of transformation images using the first and second registration processes; generating first and second motion-corrected images based on the calculated average; and comparing the first and second motion-corrected images.

Another aspect of the present invention provides an MR imaging apparatus for compensating for tissue motion during MR imaging. The MR imaging apparatus includes a scanner and a data acquisition module. The data acquisition module includes at least one control algorithm programmed to acquire a plurality of short-time MR scan images; select a reference scan image from the acquired plurality of short-time MR scan images; define a set of transformation images based on the acquired plurality of short-time MR scan images other than the selected reference scan image; register the reference scan image and the defined set of transformation images; calculate an average of aligned, registered images of the defined set of transformation images; and generate a motion-corrected image based on the calculated average.

BRIEF DESCRIPTION OF THE DRAWINGS

The above and other aspects, features, and advantages of certain embodiments of the present invention will be more apparent from the following detailed description taken in conjunction with the accompanying drawings, in which.

DETAILED DESCRIPTION OF EMBODIMENTS OF THE PRESENT INVENTION

Various embodiments of the present invention will now be described in detail with reference to the accompanying drawings. In the following description, specific details such as detailed configuration and components are merely provided to assist the overall understanding of these embodiments of the present invention. Therefore, it should be apparent to those skilled in the art that various changes and modifications of the embodiments described herein can be made without departing from the scope and spirit of the present invention. In addition, descriptions of well-known functions and constructions are omitted for clarity and conciseness.

As noted above, an MR imaging method that uses short-time scan acquisition and deformable registration to compensate for bladder motion during MR imaging is useful to evaluate and/or detect bladder cancer, and such a method is herein described.

Figure 1:
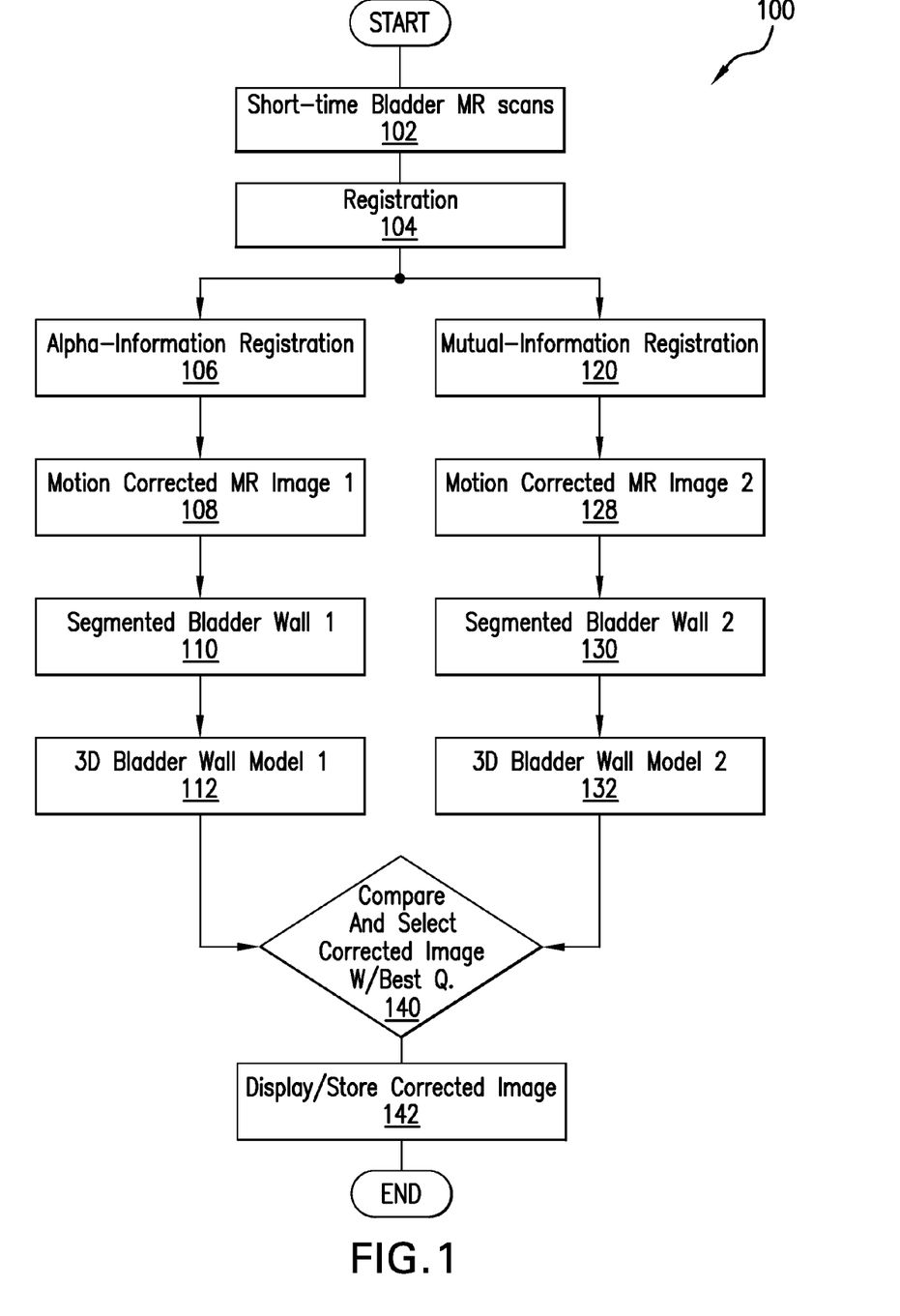
FIG. 1 is a flow chart illustrating a method for compensating for tissue motion during MR imaging, according to an embodiment of the present invention.

FIG. 1 is a flowchart illustrating a method 100 for compensating for voluntary and/or non-voluntary tissue motion during MR imaging, e.g., MR Cystography, according to an embodiment of the present invention. Voluntary motions, which are related to the unpredictable patient movements, and involuntary motions, which are related to heart beat, lung breath, etc., are problematic during MR imaging.

The method 100 uses a control algorithm embodied in an MR imaging apparatus, e.g., a 3T whole body MR scanner with a pulse sequence (or data acquisition), to mitigate motion artifacts during MR imaging, thereby obtaining an MR image having high spatial resolution on borders of the MR image, while maintaining adequate SNR.

The method 100, which compensates for motion of rigid or non-rigid tissue, is described herein in the context of compensating for motion of non-rigid tissue, e.g., a bladder. The method 100 is also usable to compensate for motion of the heart, blood vessels, lung, and colon, which are also considered to be non-rigid tissue.

Continuing with reference to FIG. 1, at step 102, a plurality of short-time MR scan images of the bladder wall of a subject, i.e., patient, were acquired using the MR scanner. In this step, to obtain an adequate tradeoff between the bladder wall outline and SNR level in the short-time acquisitions, the control algorithm uses an MR scanning protocol that includes $T_1$- and $T_2$-weighted imaging. In accordance with the present invention, both $T_1$ and $T_2$ imaging can be acquired without exogenetic contrast medium and is a fully non-invasive procedure.

Figure 2A:
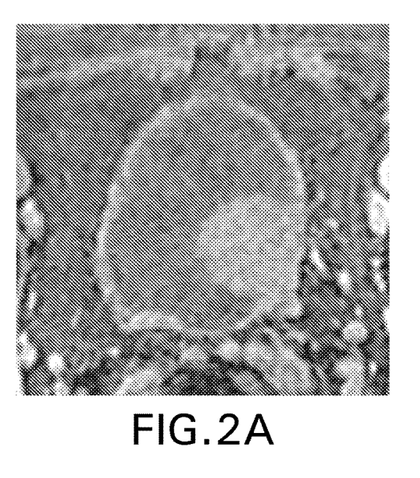
FIGS. 2A and 2B are MR images of a slice of a bladder wall that has been T1-weighted and T2-weighted, respectively, according to an embodiment of the present invention.
Figure 2B:
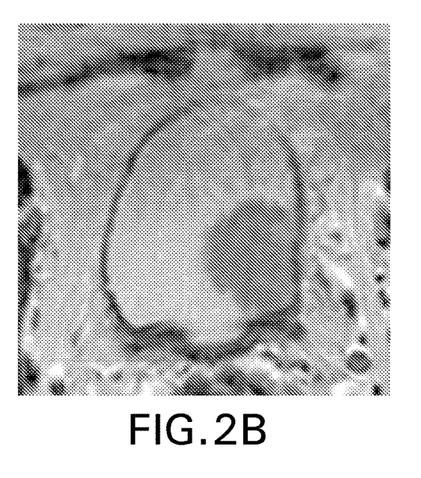

Considering two main advantages, i.e., shorter scan time and less Partial Volume (PV) influence on the inner border of the wall, of $T_1$-weighted imaging over $T_2$-weighted imaging, the $T_1$-weighted MR scans were used for delineating the bladder wall. In general, because the $T_1$-weighted imaging takes less time and gains contrast by lowering the lumen intensity, the desired signals or bladder wall are enhanced, as shown in FIG. 2A, when using $T_1$-weighted imaging. In contrast, $T_2$-weighted imaging increases or enhances the image intensities of the lumen, which tends to swallow small abnormalities on the bladder border due to the PV effect, as shown in FIG. 2B.

In embodiments of the present invention, the $T_1$-weighted imaging can be used to facilitate bladder wall extraction, while the $T_2$-weighted images provide good pathological information about the tumor invading the wall and can be used for wall analysis after the bladder extraction. Other MR images, such as diffusion weighted imaging images, dynamical enhanced imaging images, can also be used for wall analysis after the bladder extraction.

To demonstrate effectiveness of the method 100 of the present invention, prior to the performing the short-time scans, the subject was asked to empty their bladder and drink a bottle of water to allow urine to fill in their bladder. Accordingly, during the short-time scanning, the bladder was caused to slowly stretch by urine inflow.

Depending on the type of tissue being imaged, the amount of short-time scan images acquired can vary. Empirical testing found that acquiring five to eight repeated short-time scan images is adequate to image the bladder, and that acquiring six repeated short-time scans provides optimal compensation for bladder motion, with gain after averaging over six repeated short-time scans being inappreciable. In other words, increasing the time to acquire more than six short-time scans sacrifices computing efficiency.

In an embodiment of the present invention, the control algorithm was programmed to acquire six short-time scans, e.g., a number of acquisitions equal to 6, at an image array of 224×224×84 with voxel size of 0.9375×0.9375×1.0 mm³. The acquisition time for a single short-time scan was set to approximately one minute. The image array size can increase or decrease as the patient size increases or decreases, and acquisition time can correspondingly increase or decrease.

During MR imaging, the voluntary and involuntary motions described above can cause motion artifacts, which can dramatically decrease high spatial resolution on the borders of the bladder wall and SNR on the bladder wall.

FIGS. 3A-3J illustrate the effects of motion artifacts caused by voluntary and/or involuntary motion of the subject during MR imaging.

Figure 3A:
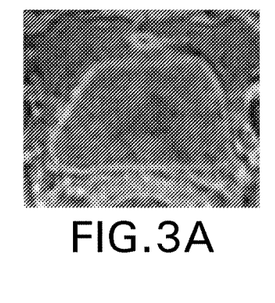
FIGS. 3A-3D are images of slices of two short-time acquisitions of a bladder wall.
Figure 3B:
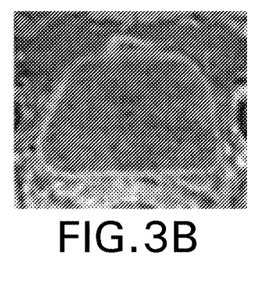
Figure 3C:
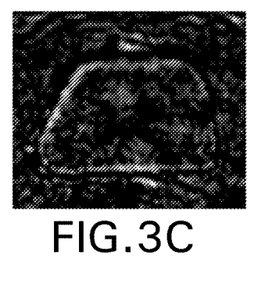
Figure 3D:
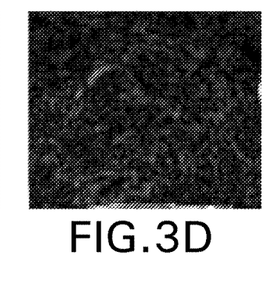
Figure 3E:
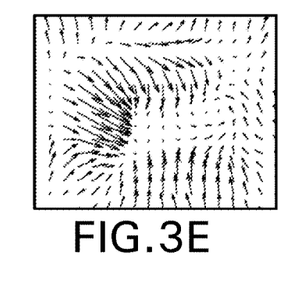
FIG. 3E illustrates deformation based on data provided from the image of FIG. 3D, according to an embodiment of the present invention.

FIGS. 3A-3B illustrate slices of two short-time acquisitions taken from volunteer studies. FIG. 3C illustrates residual noise after subtraction of data points in FIG. 3B from data points in FIG. 3A, without registration. FIG. 3D illustrates a residual slice after subtraction of data points in FIG. 3B from data points in FIG. 3A, after registration, with FIG. 3E providing deformation based on subtraction of data points in FIG. 3B from data points in FIG. 3A.

Figure 3F:
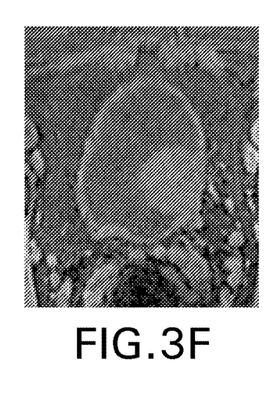
FIGS. 3F-3I are images of other slices of two short-time acquisitions of a bladder wall.
Figure 3G:
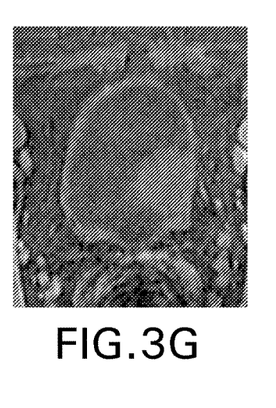
Figure 3H:
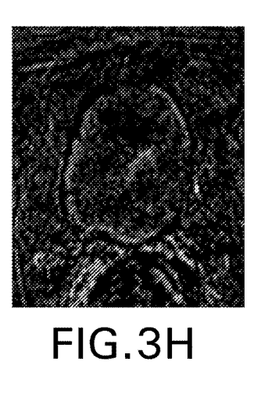
Figure 3I:
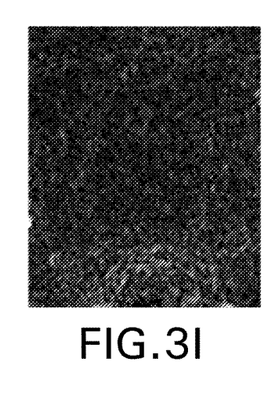
Figure 3J:
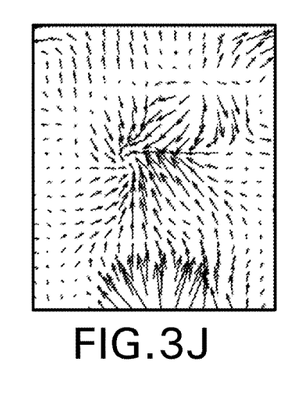
FIG. 3J illustrates deformation based on data provided from the image of FIG. 3I, according to an embodiment of the present invention.

FIGS. 3F-3G illustrate slices of two short-time acquisitions obtained from patient studies. FIG. 3H illustrates a residual slice after subtraction of data points in FIG. 3G from data points in FIG. 3F, without registration, with FIG. 3I being the residual after subtraction of data points in FIG. 3G from data points in FIG. 3F, after registration. FIG. 3J illustrates deformation based on the subtraction of data points in FIG. 3G from data points in FIG. 3F.

The corresponding difference images without registration are shown in FIGS. 3C and 3H, which show residuals of underlying noise of image acquisition and an effect of mis-registration due to bladder motion, which is clearly visible among the short-time acquisitions. FIGS. 3D and 3I show difference images after registration, showing bladder motions, e.g., involuntary or voluntary, being dramatically mitigated after registration. Accordingly, empirical testing when the motion artifact is present shows that aligning and averaging multiple short-time acquisitions enhances image quality of a final image.

Accordingly, once the plurality of short-time MR scan images are acquired, a reference scan image ($I_r$) is selected from the acquired plurality of short-time MR scan images. Additionally, a set of transformation images $T_k$ $\{T_k:x=T_k(x_r), k=1, 2, \ldots N-1\}$ is defined with the remaining acquired plurality of short-time MR scan images.

At step 104 of FIG. 1, the control algorithm registers the selected reference scan image ($I_r$) and defined set of transformation images $T_k$ via one or more registration processes.

For example, the control algorithm of the present invention may use an α-information registration process in step 106. In the α-information registration process, the control algorithm uses the defined set of transformations $T_k$ to align points of each of the acquired plurality of short-time MR scan images, e.g., $I_k$, in the defined set of transformation images $T_k$ to points in the reference scan image ($I_r$). A combined transformation model, which includes a global transformation and a local transformation, is then calculated using Equation (1):

$$T_k(x) = T_{k,global}(x) + T_{k,local}(x), \quad (1)$$

where $T_{k, global}(x)$ denotes an affine transformation, which has twelve degrees of freedom, describing the overall bladder wall motions such as the rotations, translations and scaling; and $T_{k, local}(x)$ represents a local transformation for capturing the local deformations of the bladder wall.

$T_{k, local}(x)$ was parameterized using a Free-Form Deformation (FFD) model based on B-splines, e.g., cubic or linear B-splines, suitable for modeling three-dimensional deformations. A B-splines-based FFD model was chosen because the B-splines-based FFD model possesses superior local support nature, general applicability and computational efficiency, was used, with the FFD model preferably based on cubic B-splines.

The control algorithm uses the FFD model to deform an image, e.g., one of the short-time scanned images, by manipulating a regular mesh of control points distributed across the entire image. The deformation result of the mesh can then be applied to generate a smooth and $C^2$ continuous transformation. $C^n$ is a parametric continuity used to describe the smoothness of a parametric curve. The n represents the continuity order of a curve. A curve can be said to have $C^n$ continuity, if its n order of derivatives is continuous of value throughout the curve. $C^2$ represents the first and second derivatives of the parametric curve, generated by the transformation, and is continuous. The degree of the deformation is determined by the spacing of the control point mesh.

The control algorithm calculates $T_{k, local}(X)$ using parameters of Φ, which represents a $n_x \times n_y \times n_z$ grid of control points $\phi_{i,j,k}$ with uniform spacing, and degree (d) of cubic B-splines of three. Thus, at any position x, the FFD can be written as a three dimensional tensor product of a one dimensional cubic B-splines using Equation (2):

$$T_{local}(x) = \sum_{l=0}^{3} \sum_{m=0}^{3} \sum_{n=0}^{3} B_l(u) B_m(v) B_n(w) \phi_{i+l, j+m, k+n}, \quad (2)$$

where $$i = \left\lfloor \frac{x}{n_x} \right\rfloor - 1, \, j = \left\lfloor \frac{y}{n_y} \right\rfloor - 1, \, k = \left\lfloor \frac{z}{n_z} \right\rfloor - 1,$$

$$u = \frac{x}{n_x} - \left\lfloor \frac{x}{n_x} \right\rfloor, \, v = \frac{y}{n_y} - \left\lfloor \frac{y}{n_y} \right\rfloor, \, w = \frac{z}{n_z} - \left\lfloor \frac{z}{n_z} \right\rfloor$$

and $B_l$ denotes the $l_{th}$ basis function of the B-spline further to Equation (3):

$$B_0(u) = (1-u)^3/6$$

$$B_1(u) = (3u^3 - 6u^2 + 4)/6$$

$$B_2(u) = (-3u^3 + 3u^2 + 3u + 1)/6$$

$$B_3(u) = u^3/6 \quad (3)$$

The above registration process aligns the reference scan image ($I_r$) with each of the acquired plurality of short-time MR scan images in the set of transformations $T_k$ so that an average of the aligned scan images, preferably points of the aligned images, can be determined, as described below.

To increase accuracy of the α-information registration at step 106, the control algorithm performs cost function analysis or a similarity measure based on the negative of the α-information, which is a special case of a-divergence and measures the distance between the joint probability p of two variables and their marginal probabilities' product $Q = P_1 \times P_2$, with a definition of a-information provided by Equation (4):

$$I_\alpha(P, P_1 \times P_2) = \frac{1}{a(a-1)} \left( \sum_{i,j} \frac{p_{ij}^\alpha}{(p_i p_j)^{\alpha-1}} - 1 \right), \quad (4)$$

where $\alpha \neq 0, 1$.

When $a \to 1$, Equation (4) can be rewritten as Equation (5):

$$I_1(P, P_1 \times P_2) = \sum_{i,j} p_{ij} \log\left(\frac{p_{ij}}{p_i p_j}\right) \quad (5)$$

When $a \to 1$, Equation (5) becomes the definition of mutual-information that is used with a mutual-information registration process.

C(u,a) between the reference scan image ($I_r$) and a moving image (i.e., the acquired plurality of short-time MR scan images in the defined set of transformation images $T_k$) can be expressed by the transformation parameters u and a in Equation (6):

$$C(u, a) = -\frac{1}{a(a-1)} \left( \sum_{l,k} \frac{p^{(a)}(l, k \mid u)}{(p_M(l \mid u) p_R(k))^{a-1}} - 1 \right), \quad (6)$$

where $p^{(a)}$, $p_M$ and $p_R$ are joint, marginal moving, and marginal reference probability distributions, respectively, and u represents parameters of the transformation. It was assumed that HR and HM represented specified numbers of uniformly sized bins along respective dimensions of a joint histogram of the reference signal image ($I_r$) and moving images (e.g., the acquired plurality of short-time MR scan images in the defined set of transformation images $T_k$). Accordingly, integer values l and k can then be denoted with indexes of histogram bins, i.e., ($0 \leq k < H_R$, $0 \leq l < H_M$).

A Parzen window may be used to estimate the underlying image intensity distributions for smoothing the underlying image. In particular, regarding Equation 6, the estimation of the marginal and joint probability distributions of the intensity value of the reference scan image ($I_r$) and the moving image (e.g., the acquired plurality of short-time MR scan images in the set of transformation images $T_k$) is required. The Parzen window, a kernel density estimation method, is used to estimate those probability distributions, i.e. $p^{(a)}$, $p_M$ and $p_R$ in Equation 6. Using the Parzen window can generate continuous estimations of the above probability distributions, and thereby reduce the effects of quantization from interpolation and discretization from binning data.

Moreover, optimizing the cost function may prove useful, and a Limited-Memory Broyden-Fletcher-Goldfarb-Shanno (L-BFGS) is a preferred method used to optimize the cost function. For a set of n-independent parameters, the gradient of α-information is given as $$\nabla C = \left[ \frac{\partial C}{\partial \mu_1}, \frac{\partial C}{\partial \mu_2}, \ldots, \frac{\partial C}{\partial \mu_i}, \ldots, \frac{\partial C}{\partial \mu_n} \right],$$

whose i-th derivative is calculated using Equation (7):

$$\frac{\partial C}{\partial \mu_i} = -\frac{1}{\alpha(\alpha-1)} \sum_{l,k} \frac{\alpha p^{\alpha-1}(l,k|\mu) \frac{\partial p(l,k|\mu)}{\partial \mu_i} - (\alpha-1) p^{\alpha}(l,k|\mu) p_M^{-1}(l|\mu) \sum_k \frac{\partial p(l,k|\mu)}{\partial \mu_i}}{[p_M(l|\mu) p_R(k)]^{\alpha-1}} \quad (7)$$

The L-BFGS method was chosen because the L-BFGS method possesses high dimensionability of the parameter space and allows bound constraints of the variables.

After the reference scan image ($I_r$) is aligned with each of the acquired plurality of short-time MR scan images in the defined set of transformations $T_k$, an average of the aligned, registered short-time MR scan images is calculated. Calculating an average of the aligned, registered images in the defined set of transformation images $T_k$ at this juncture in MR imaging, i.e., after alignment, is different from conventional methods, which typically calculate a direct average of the acquired short-time MR scan images, i.e., an average that is calculated immediately after the short-time MR scan images are acquired.

Thereafter, at step 108 of FIG. 1, a motion-corrected image 1 based on the calculated average of the aligned, registered images in the defined set of transformation images $T_k$ is generated.

The control algorithm performs image segmentation on the motion-corrected image 1 at step 110 (FIG. 1) to measure thickness of an inner border of the bladder wall. Then, at step 112, the control algorithm performs thickness mapping of the inner border for detecting bladder tumors on the bladder wall.

At step 120 of FIG. 1, a mutual-information registration process is performed based on reference scan image ($I_r$), as described above at step 104.

The mutual-information registration process at step 120 uses a mutual-information registration based model that is based on a maximization of an images' mutual-information in combination with a parameterized deformation field that is similar to the B-splines based FFD model described in regards to step 106. The mutual-information registration process performed at step 120 averages the acquired short-time scan images after registration, and may not perform as well as the α-information registration process at step 106 since elastic properties of bladder tissue can differ between patients and age groups. Accordingly, the mutual-information registration process at step 120 may be not be optimal for use with bladder MR imaging, particularly when a tumor or other anomaly is present in the bladder wall. Accordingly, the mutual-information registration process at step 120 of FIG. 1 may be reserved to image rigid tissue.

In step 128 of FIG. 1, after the mutual-information registration process 120, a motion-corrected image 2 is generated based on the registered short-time MR scan images. Image segmentation on the motion-corrected image 2 is then performs at step 130 to measure thickness of an inner border of the bladder wall. Then, at step 132, the control algorithm performs thickness mapping of the inner border for detecting bladder tumors on the bladder wall.

At step 140 of FIG. 1, the control algorithm calculates a quality of each of the corrected-images 1, 2 output from steps 112 and 132, respectively, and a best quality corrected image is selected.

Mean and variance of a Squared Sum of intensity Differences (SSD) and the Correlation Coefficient (CC) of each of the corrected images are calculated using Equations (8) and (9):

$$SSD = \frac{1}{n} \sqrt{\sum (F_R - T(F_M))^2} \quad (8)$$

$$CC = \frac{\sum (F_R - \overline{F}_R)(T(F_M) - T(\overline{F}_M))}{\sqrt{\sum (F_R - \overline{F}_R)^2 \sum (T(F_M) - T(\overline{F}_M))^2}} \quad (9)$$

where $\overline{F}_R$ and $\overline{F}_M$ represent average intensities of reference scan image ($I_r$) and moving image, respectively, e.g., the acquired plurality of short-time MR scan images in the set of transformation images $T_k$; with the SSD and CC providing a direct measure of corrected image quality, i.e., quality of the registration processes.

At step 142 of FIG. 1, the best quality corrected image is output, and can be stored in memory of the MR imaging scanner for future clinician access or directly transmitted to a display.

As noted above, the bladder is non-rigid and the corrected image 1 output from Step 112 of FIG. 1 will typically have best quality and an embodiment therefore implement only the α-information registration process. That is, at step 102, a plurality of short-time MR scan images are acquired, reference scan image ($I_r$) is selected from the acquired plurality of short-time MR scan images, and a set of transformation images $T_k$ based on the acquired plurality of short-time MR scan images other than the selected reference scan image is defined. At steps 104/106, the reference scan image (I$_r$) and the defined set of transformation images T$_k$ are registered, and an average of aligned, registered images of the defined set of transformation images T$_k$ is calculated, followed by generating a motion-corrected image 1 based on the calculated average at step 108 and quality control at step 140 using SSD and CC, as described above, to determine whether corrected-image 1 meets a predetermined quality value.

If the corrected image meets the predetermined quality value, the corrected image 1 is displayed/stored at step 142. If the corrected image 1 does not meet the predetermined quality value, the process returns back to step 102, to repeat the a-information registration process, thereby providing a clearer and more robust motion-corrected image than available utilizing conventional MR imaging methods that short-time scan without averaging after registration or long-time scan utilizing other registration processes.

Figure 4A:
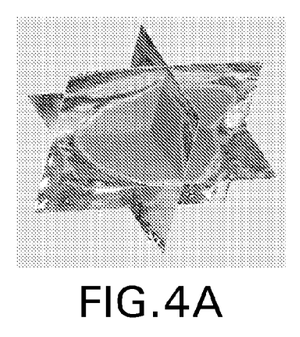
FIG. 4A is a three-dimensional graph illustrating acquired volumes in three standard image acquisition orientations, according to an embodiment of the present invention.

FIG. 4A is a three-dimensional graph illustrating acquired volumes in three standard image acquisition orientations, according to an embodiment of the present invention; and FIGS. 4B-4G provide a comparison of images taken between the average of motion-corrected short-time acquisitions obtained in accordance with the method 100 of the present invention and an equivalent long-time acquisition with signal average (LTASA) taken with a conventional MR scanner. The LTASA taken by the MR scanner is a k-space average controlled by an integer value of parameter NSA obtained by averaging multiple measurements in the k-space before image reconstruction.

Figure 4B:
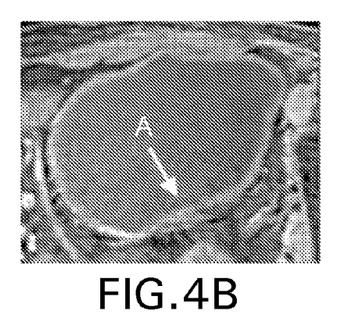
FIGS. 4B-4D are images of a bladder wall slice obtained using long-time acquisition with signal average.
Figure 4C:
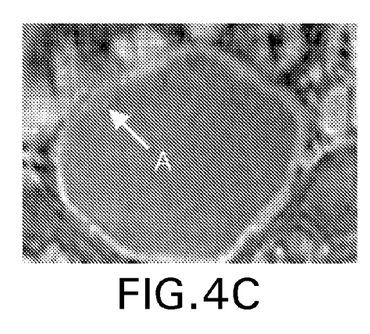
Figure 4D:
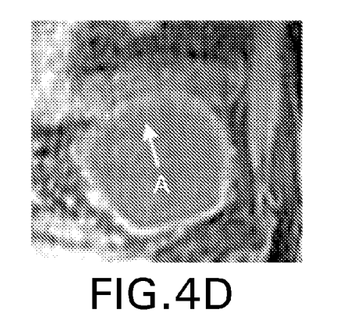
Figure 4E:
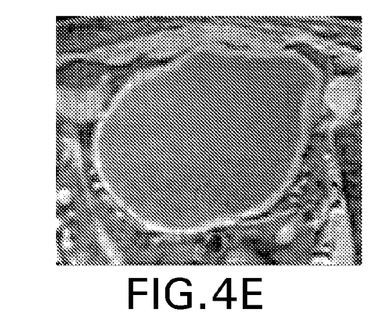
FIGS. 4E-4G are images of a bladder wall slice obtained using an average of motion-corrected short-time acquisitions, according to an embodiment of the present invention.
Figure 4F:
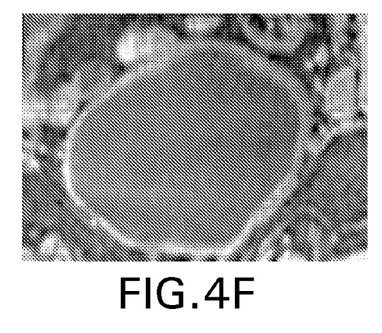
Figure 4G:
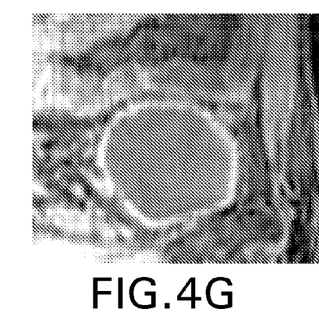

The motion-corrected average obtained in accordance with the present invention and the LTASA obtained by the MR scanner were taken in three standard image acquisition orientations, i.e., transverse, coronal and sagittal, shown in FIG. 4A. FIGS. 4B-4D show edge blurring ("A") that is present in conventional long-time acquisition. In contrast, method 100 of the present invention performs motion correction that more clearly defines the bladder wall in terms of edge details and wall uniformity, as shown in FIG. 4E-4G.

Figure 5A:
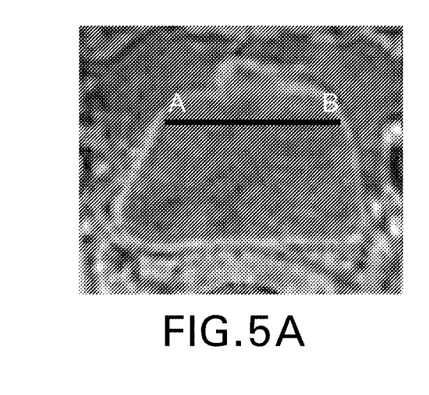
FIG. 5A is an image of a slice of a bladder wall obtained using a short-time acquisition without signal average, according to an embodiment of the present invention.
Figure 5B:
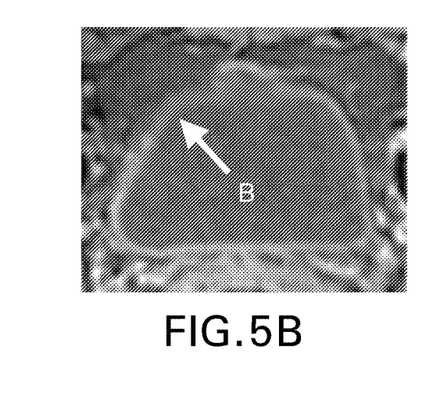
FIG. 5B is an image of a slice of a bladder wall obtained using an average of six short-time acquisitions without motion correction, according to an embodiment of the present invention.
Figure 5C:
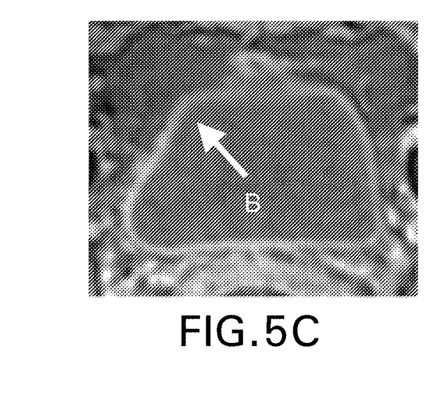
FIG. 5C is an image of a slice of a bladder wall obtained using an average after motion correction, according to an embodiment of the present invention.

FIGS. 5A-5L illustrate gain obtained in enhancing edge details, while preserving SNR, or enhancing SNR and preserving edge details, utilizing method 100 of the present invention. FIGS. 5A-5C are short-time scan images, with FIG. 5A illustrating a short-time acquisition without signal averaging (segment of a slice), FIG. 5B illustrating the average of six short-time acquisitions without motion correction, and FIG. 5C illustrating an average after motion correction using the method 100.

Figure 5D:
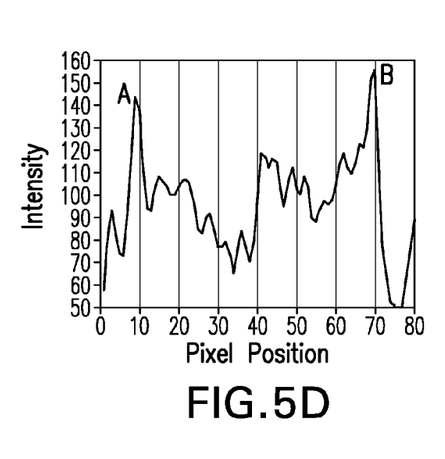
FIGS. 5D-5F are graphs illustrating intensity profiles based on image positions indicated by line segment "A-B" of FIG. 5A.
Figure 5E:
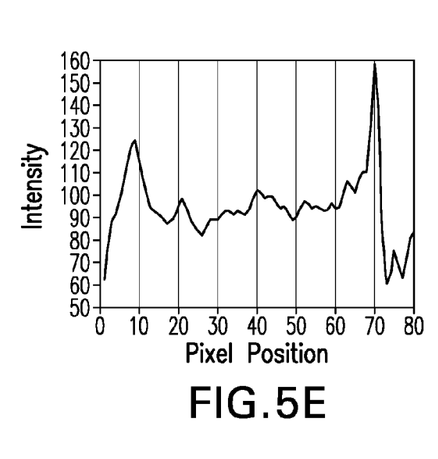
Figure 5F:
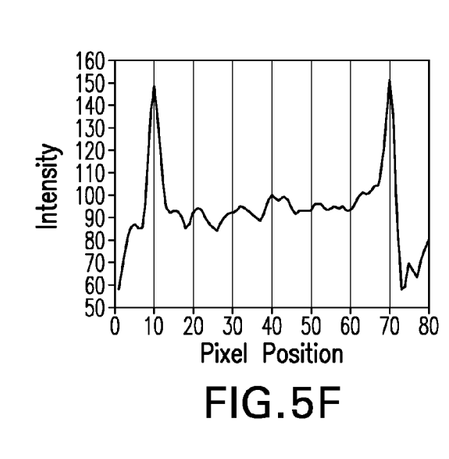

FIGS. 5D-5F are intensity profiles based on image positions indicated by the line segment "A-B" shown in FIG. 5A. Bladder wall edge blurring is indicated at "B" in FIGS. 5B-5C. Labels "A" and "B" in FIG. 5D correspond to positions "A-B" of FIG. 5A.

Figure 5G:
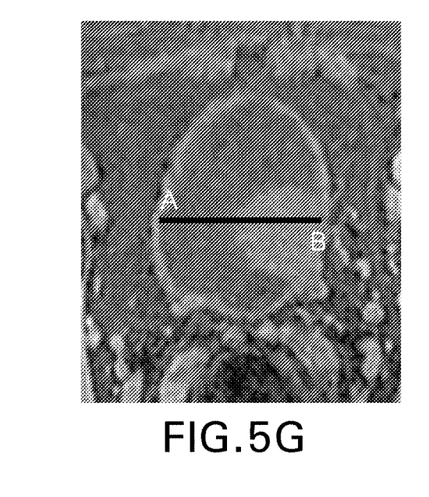
FIG. 5G is an image of a slice of a bladder wall obtained using a short-time acquisition without signal average, according to an embodiment of the present invention.
Figure 5H:
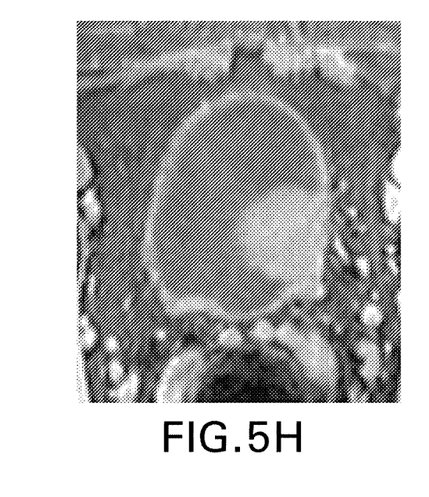
FIG. 5H is an image of a slice of a bladder wall obtained using an average of six short-time acquisitions without motion correction.
Figure 5I:
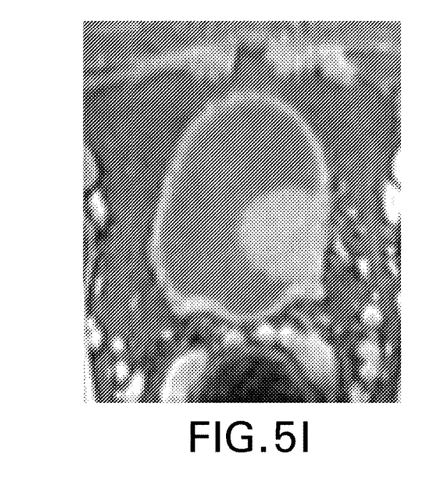
FIG. 5I is an image of a slice of a bladder wall using an average after motion correction, according to an embodiment of the present invention.

FIGS. 5G-5I are short-time scan images, with FIG. 5G illustrating short-time acquisition without signal averaging; FIG. 5H illustrating an average of six short-time acquisitions without motion correction; and FIG. SI illustrating an average with motion correction using the method 100 according to the present invention.

Figure 5J:
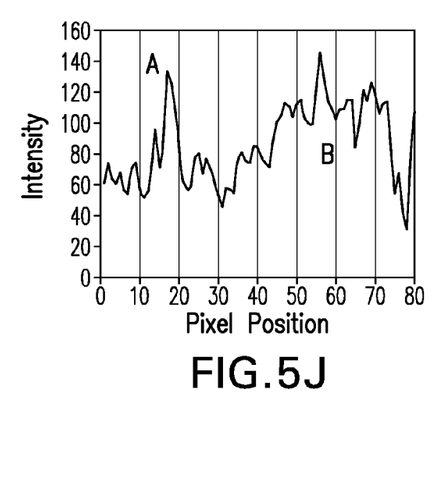
FIGS. 5J-5L are graphs illustrating intensity profiles based on image positions indicated by the line segment "A-B" of FIG. 5G, according to an embodiment of the present invention.
Figure 5K:
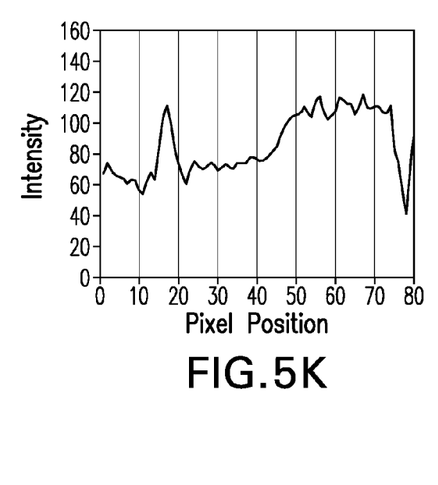
Figure 5L:
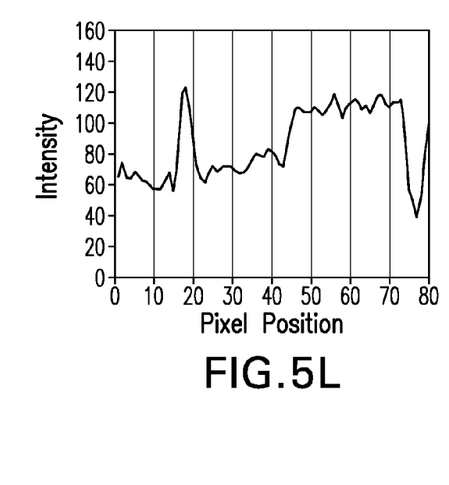

FIGS. 5J-5L are intensity profiles based on image positions indicated by line segment "A-B" of FIG. 5G, with "A" indicating a bladder wall position and label "B" representing a bladder wall tumor.

FIGS. 5A-5L indicate that averaging multiple short-time acquisitions of the present invention enhances the SNR, as compared to the conventional short-time acquisitions. The averaged image with motion correction better preserved bladder wall definition than the averaged image without motion correction; and the bladder walls were blurred without the motion correction of the present invention.

Empirical testing also shows that gain of SNR during the a-information registration and mutual-information registration processes is maintained, if not increased, when compared to conventional MR imaging. It is noted that since the bladder lumen is the only uniform region in the bladder, the signal was measured from the bladder lumen, and noise was measured from a no-signal region outside of the bladder. Based on the method of Henkelman and Kaufman, et al., the SNR value can be calculated using Equation (10):

$$SNR = \frac{u_{signal}}{1.5 \times \sigma_{noise}}, \qquad (10)$$

where u$_{signal}$ denotes the mean of signal and σ$_{noise}$ denotes the standard deviation of noise. Since the noise was measured in a no-signal region where noise follows Rician distribution rather than Gaussian distribution, a factor of 1.5 was included to account for underestimation of σ$_{noise}$ when measured in air in a magnitude MR image.

SNR values measured by mean+/−standard deviations for five patients are listed in Table 1, which shows that the measured SNR increased with the increment of the number of acquisitions in the average, as expected. More importantly, as compared to the long-time acquisitions, the final average of six short-time acquisitions achieved comparable and possibly higher SNR values.

TABLE 1

| SNR | Non motion correction | Motion-corrected |
|---|---|---|
| Single short-time scan | 4.42 ± 0.43 | |
| Average of 2 short-time scans | 6.21 ± 0.72 | 6.51 ± 0.97 |
| Average of 3 short-time scans | 7.57 ± 0.97 | 8.43 ± 1.40 |
| Average of 4 short-time scans | 8.19 ± 1.09 | 8.74 ± 1.46 |
| Average of 5 short-time scans | 9.28 ± 1.26 | 10.55 ± 2.33 |
| Average of 6 short-time scans | 9.56 ± 1.32 | 10.97 ± 2.42 |

Contrast to Noise ratio (CNR) values were measured with respect to the bladder wall and surroundings. Since bladder wall surroundings are complicated, the bladder lumen was used as background, and the CNR value was calculated using Equation (11):

$$CNR = \frac{|u_{wall} - u_{background}|}{\sqrt{\sigma_{wall}^2 - \sigma_{background}^2}}, \qquad (11)$$

where u$_{wall}$ and u$_{background}$ represent the means of the bladder wall and the background, respectively, and σ$_{wall}$ and σ$_{background}$ denote the standard deviations of the bladder wall and the background, respectively.

Figure 6:
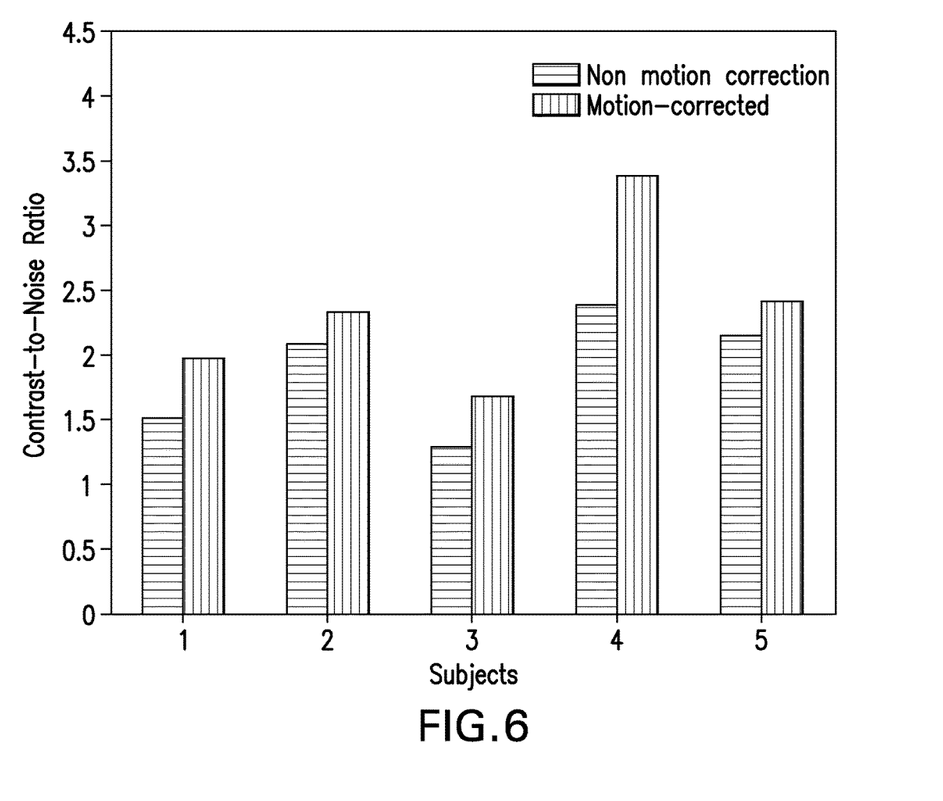
FIG. 6 is a bar graph comparing contrast to noise ratio values between a final average of five images, with and without motion correction of the present invention.

FIG. 6 compares CNR values between final averages of five images, with and without the motion correction of the present invention, showing that motion corrected averages provided by the present invention outperform averages provided without motion correction.

Accordingly, the MR imaging method 100 of the present invention provides an effective and simple way of acquiring repeated short-time acquisitions, performing non-rigid alignment of the short-time acquisitions to a selected reference, and forming a single motion-corrected average image.

The MR image method 100 of the present invention can be implemented without addition or modification of hardware, such as a specialized coil, is fully evasive, and can correct for image domain deformations, without being scan protocol specific. The MR imaging method 100 facilitates extraction of better image quality bladder wall images usable to detect bladder abnormality and provides dynamic MR imaging of other moving organs, such as heart, lungs, etc., to provide tissue contrast information inside the bladder wall for functional studies and pathological assessment.

While the present invention has been particularly shown and described with reference to certain embodiments thereof, it will be understood by those of ordinary skill in the art that various changes in form and details may be made therein without departing from the spirit and scope of the present invention as defined by the following claims and their equivalents.

What is claimed is:

1. A method for compensating for tissue motion during magnetic resonance (MR) imaging, the method comprising:
    acquiring a plurality of short-time MR scan images;
    selecting a reference scan image from the acquired plurality of short-time MR scan images;
    defining a set of transformation images based on the acquired plurality of short-time MR scan images other than the selected reference scan image;
    registering the reference scan image and the defined set of transformation images;
    calculating an average of aligned, registered images of the defined set of transformation images; and
    generating a motion-corrected image based on the calculated average.

2. The method according to claim 1, wherein registering the reference scan image and the set of defined transformation images includes aligning points in each image of the acquired plurality of short-time MR scan images in the defined set of transformation images to points in the reference scan image.

3. The method according to claim 2, wherein registering the reference scan image and the set of defined transformation images includes determining a global transformation representing an overall motion of the defined set of transformation images and a local transformation representing a local deformation of the defined set of transformation images.

4. The method according to claim 3, wherein the global transformation is a twelve parameter affine transformation.

5. The method according to claim 3, wherein the local transformation is a free form transformation based on B-splines.

6. The method according to claim 5, wherein the B-splines are one of linear B-splines and cubic B-splines.

7. The method according to claim 1, wherein registering the reference scan image and the defined set of transformation images includes performing a cost function analysis of the calculated average based on a negative of α-information between the reference scan image and the defined set of transformation images using Equation:

$$C(\mu, \alpha) = -\frac{1}{\alpha(\alpha-1)} \left( \sum_{l,k} \frac{p^{(\alpha)}(l,k|\mu)}{p_M(l|\mu)p_R(k)^{\alpha-1}} - 1 \right).$$

8. The method according to claim 7, further including optimizing the cost function analysis using Equation:

$$\frac{\partial C}{\partial \mu_i} = -\frac{1}{\alpha(\alpha-1)} \sum_{l,k} \frac{\alpha p^{\alpha-1}(l,k|\mu)\frac{\partial p(l,k|\mu)}{\partial \mu_i} - (\alpha-1)p^\alpha(l,k|\mu)p_M^{-1}(l|\mu)\sum_k \frac{\partial p(l,k|\mu)}{\partial \mu_i}}{[p_M(l|\mu)p_R(k)]^{\alpha-1}}.$$

9. The method according to claim 1, further including calculating a quality of the registration of the reference scan image and the defined set of transformation images using a Squared Sum of intensity Difference (SSD) of:

$$SSD = \frac{1}{n}\sqrt{\sum(F_R - T(F_M))^2}.$$

10. The method according to claim 9, wherein calculating the quality of the registration of the reference scan image and the defined set of transformation images includes using a Correlation of Coefficients (CC) of:

$$CC = \frac{\sum(F_R - \overline{F}_R)(T(F_M) - T(\overline{F}_M))}{\sqrt{\sum(F_R - \overline{F}_R)^2 \sum(T(F_M) - T(\overline{F}_M))^2}}.$$

11. The method according to claim 1, further including estimating underlying image intensity distributions of the registered reference scan image and the defined set of transformation images using a Parzen window.

12. The method according to claim 1, wherein a number of the acquired plurality of short-time MR scan images includes six to eight MR scan images.

13. A method for compensating for tissue motion during magnetic resonance (MR) imaging, the method comprising:
    acquiring a plurality of short-time MR scan images;
    selecting a reference scan image from the acquired plurality of short-time MR scan images;
    defining, using a first registration process, a first set of transformation images based on the acquired plurality of short-time MR scan images other than the selected reference scan image;
    defining, using a second registration process, a second set of transformation images based on the acquired plurality of short-time MR scan images other than the selected reference scan image;
    registering the reference scan image and the defined first and second sets of transformation images using the first registration process and the second registration process;
    calculating an average of aligned, registered images of the defined first and second sets of transformation images;
    generating first and second motion-corrected images based on the calculated average; and
    comparing the first and second motion-corrected images.

14. The method according to claim 13, wherein the first registration process is an α-information registration process.

15. The method according to claim 13, wherein the second registration process is a mutual-information registration process.

* * * * *

UNITED STATES PATENT AND TRADEMARK OFFICE
CERTIFICATE OF CORRECTION

PATENT NO. : 9,788,795 B2
APPLICATION NO. : 14/784192
DATED : October 17, 2017
INVENTOR(S) : Jerome Z. Liang et al.

It is certified that error appears in the above-identified patent and that said Letters Patent is hereby corrected as shown below:

In the Specification

In Column 1, please add the following after the Priority paragraph:
GOVERNMENT SUPPORT
This invention was made with government support under CA120917 awarded by the National Institutes of Health. The government has certain rights in the invention.

Signed and Sealed this
Twenty-seventh Day of November, 2018

Andrei Iancu
*Director of the United States Patent and Trademark Office*